United States Patent [19]

LeMaistre et al.

[11] 4,169,152

[45] Sep. 25, 1979

[54] ISOHEXIDE AND TETRAHYDROFURAN ETHERS AND THEIR CARBAMATES IN METHOD OF BRINGING ABOUT RELAXATION OF SKELETAL MUSCULATURE

[75] Inventors: John W. LeMaistre; Taketoshi P. Mori, both of Wilmington, Del.

[73] Assignee: ICI Americas Inc., Wilmington, Del.

[21] Appl. No.: 847,170

[22] Filed: Oct. 31, 1977

[51] Int. Cl.$^2$ .............................................. A61K 31/34
[52] U.S. Cl. .................................. 424/285; 260/347.3; 260/347.8
[58] Field of Search ................... 260/347.8, 347.3; 424/285

[56] References Cited

U.S. PATENT DOCUMENTS

| | | | |
|---|---|---|---|
| 2,234,200 | 3/1941 | Soltzberg | 260/615 |
| 2,322,820 | 6/1943 | Brown | 260/345 |
| 2,322,821 | 6/1943 | Brown | 260/345 |
| 2,387,842 | 10/1945 | Soltzberg | 260/345 |
| 2,420,519 | 5/1947 | Brown | 260/345 |
| 2,572,566 | 10/1951 | Himel et al. | 260/347.8 |
| 2,771,471 | 11/1956 | De Groote | 260/347.8 X |
| 3,225,066 | 12/1965 | Lew | 260/347.3 |
| 3,225,067 | 12/1965 | Le Maistre et al. | 260/347.4 |
| 3,225,068 | 12/1965 | Zech | 260/347.4 |
| 3,272,845 | 9/1966 | Zech | 260/347.8 |
| 3,342,680 | 9/1967 | Treon | 167/65 |
| 3,671,458 | 6/1972 | Sherman et al. | 252/351 |
| 3,671,550 | 6/1972 | Hagemeyer et al. | 260/347.8 |
| 3,734,929 | 5/1973 | Robinson | 260/347.8 X |

Primary Examiner—Richard Raymond

[57] ABSTRACT

Disclosed are isohexide and tetrahydrofuran ethers and their carbamates and pharmaceutical compositions thereof and related compounds that exhibit central nervous system depressant activity, particularly skeletal muscle relaxant activity.

8 Claims, No Drawings

ISOHEXIDE AND TETRAHYDROFURAN ETHERS AND THEIR CARBAMATES IN METHOD OF BRINGING ABOUT RELAXATION OF SKELETAL MUSCULATURE

The present invention relates to certain isohexide and tetrahydrofuran ethers and their carbamates which demonstrate central nervous system depressant activity in living animals, particularly skeletal muscle relaxant activity in living animals.

The principal object of the present invention is to provide compounds which are quite specific in their skeletal muscle relaxant activity in living animals, more particularly mammalians, and which can be taken orally. Other objects will also be evident from the following more detailed description of the invention.

The novel compounds of this invention may be structurally illustrated by the following formulas:

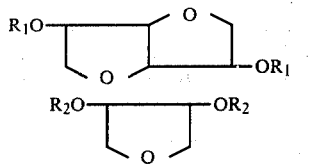

wherein each $R_1$ is a radical independently selected from the group consisting of hydrogen, aryl, aralkyl where the aralkyl radical contains from 9 to 12 carbon atoms, alkyl substituted aryl, haloalkyl substituted aryl, alkoxy substituted aryl, halogen substituted aryl, alkyl substituted aralkyl, haloalkyl substituted aralkyl, alkoxy substituted aralkyl, mono-halogen substituted aralkyl where the aralkyl radical contains from 7 to 12 carbon atoms, di- and tri-halogen substituted aralkyl where the aralkyl radical contains 9 to 12 carbon atoms, and

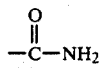

and each $R_2$ is independently selected from the group consisting of hydrogen, aryl, aralkyl, alkyl substituted aryl, haloalkyl substituted aryl, alkoxy substituted aryl, halogen substituted aryl, alkyl substituted aralkyl, haloalkyl substituted aralkyl, alkoxy substituted aralkyl, halogen substituted aralkyl, and

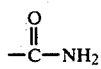

with the proviso that at least one $R_1$ and $R_2$ in each formula is other than hydrogen or

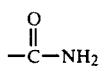

For purposes of exemplification and not limitation, the above radicals designated $R_1$ and $R_2$ in relation to formulas (a) and (b) above, and the radicals designated $R_3$ and $R_4$ in relation to formulas (c) and (d) below, unless indicated otherwise, include the following within their scope. The term "aryl" as used hereinabove includes the radicals phenyl and naphthyl. The term "aralkyl" includes such radicals derived from phenyl and naphthyl radicals wherein the alkyl portion of the radical contains from one to ten carbon atoms, for example, benzyl, phenethyl, methylbenzyl, 3-naphthylethyl and 3-phenylpropyl. The terms "alkyl substituted aryl" and "alkyl substituted aralkyl" are used herein to denote any aryl or aralkyl radical as defined above substituted with straight or branch chain alkyl groups containing from one to ten carbon atoms. When halogen is referred to in relation to any of the radicals represented by $R_1$, $R_2$, $R_3$ and $R_4$ herein, all halogens having an atomic weight up to 127 are intended, and thus, fluorine, chlorine, iodine, and bromine are included; however, fluorine, chlorine, and bromine are preferred. The terms "haloalkyl substituted aryl" and "haloalkyl substituted aralkyl" are used herein to denote aryl and aralkyl radicals as defined above substituted with at least one and no more than three haloalkyl radicals, each of which contains from one to ten carbon atoms and at least one and no more than six halogen atoms. "Alkoxy substituted aryl" and "alkoxy substituted aralkyl" are used herein to describe aryl and aralkyl radicals as indicated above substituted with at least one and no more than three alkoxy radicals each of which contains from one to ten carbon atoms. The terms "halogen substituted aryl" and "halogen substituted aralkyl" are used herein to denote aryl and aralkyl radicals as defined above which are substituted with at least one and no more than five halogen atoms, preferably one to three halogen atoms.

As indicated above, the novel compounds of the present invention exhibit skeletal muscle relaxant activity in living animals, more particularly, mammalian animals. These compounds can be utilized for therapeutic use when they are suitably compounded into pharmaceutical preparations such as tablets, capsules, elixirs, suspensions, parental solutions or suspensions, and suppositories or the like by known pharmaceutical techniques.

As noted, the compounds of the invention are characterized by their central nervous depressant activity, especially skeletal muscle relaxant effect. Monoethers (i.e., compounds of formula (a) and (b) above and (c) and (d) below, where one $R_1$, $R_2$, $R_3$ or $R_4$ is hydrogen) demonstrate the best activity and are preferred. However, useful effects are also obtainable with the diethers.

In a preferred subclass of the present invention, $R_1$ is a radical independently selected from the group consisting of hydrogen, phenyl, phenylalkyl ($C_3$ to $C_6$), alkyl ($C_1$ to $C_6$) substituted phenyl, haloalkyl ($C_1$ to $C_6$) substituted phenyl, alkoxy ($C_1$ to $C_6$) substituted phenyl, halogen, substituted phenyl, alkyl ($C_1$ to $C_6$) substituted phenylalkyl ($C_1$ to $C_6$) where the substitution is on the phenyl ring, haloalkyl ($C_1$ to $C_6$) substituted phenylalkyl ($C_1$ to $C_6$) where the substitution is on the phenyl ring, alkoxy ($C_1$ to $C_6$) substituted phenylalkyl ($C_1$ to $C_6$) where the substitution is on the phenyl ring, monohalogen substituted benzyl where the substitution is on the phenyl ring, and di- and tri-halogen substituted phenylalkyl ($C_3$ to $C_6$) where the substitution is on the phenyl ring, and

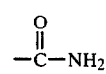

with the proviso that at least one $R_1$ is other than hydrogen or

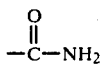

In a further preferred subclass of the present invention, each $R_1$ is a radical independently selected from the group consisting of hydrogen, phenyl, phenylpropyl, phenylbutyl, mono-alkyl ($C_1$ to $C_4$) substituted phenyl, mono-haloalkyl ($C_1$ to $C_4$) substituted phenyl, mono-alkoxy ($C_1$ to $C_4$) substituted phenyl, mono-halogen substituted phenyl, mono-alkyl ($C_1$ to $C_4$) substituted phenylalkyl ($C_1$ to $C_4$) where the substitution is on the phenyl ring, mono-haloalkyl ($C_1$ to $C_4$) substituted phenylalkyl ($C_1$ to $C_4$) where the substitution is on the phenyl ring, mono-alkoxy ($C_1$ to $C_4$) substituted phenylalkyl ($C_1$ to $C_4$) where the substitution is on the phenyl ring, mono-halogen substituted phenylalkyl ($C_1$ to $C_4$) where the substitution is on the phenyl ring, and

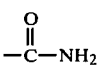

with the proviso that at least one $R_1$ is other than hydrogen or

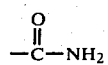

In another preferred subclass of the present invention, each $R_1$ is a radical independently selected from the group consisting of hydrogen, phenyl, phenylpropyl, mono-methyl substituted phenyl, mono-trifluoromethyl substituted phenyl, mono-methoxy substituted phenyl, mono-fluoro substituted phenyl, mono-chloro substituted phenyl, mono-methyl substituted benzyl where the substitution is on the phenyl ring, mono-trifluoromethyl substituted benzyl where the substitution is on the phenyl ring, mono-alkoxy substituted benzyl where the substitution is on the phenyl ring, mono-fluoro substituted benzyl where the substitution is on the phenyl ring, mono-chloro substituted benzyl where the substitution is on the phenyl ring, and

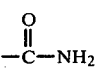

with the proviso that at least one $R_1$ is other than hydrogen or

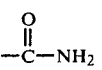

In a preferred subclass of the present invention each $R_2$ is a radical independently selected from the group consisting of hydrogen, phenyl, phenylalkyl ($C_1$ to $C_6$), alkyl ($C_1$ to $C_6$) substituted phenyl, haloalkyl ($C_1$ to $C_6$) substituted phenyl, alkoxy ($C_1$ to $C_6$) substituted phenyl, halogen substituted phenyl, alkyl ($C_1$ to $C_6$) substituted phenylalkyl ($C_1$ to $C_6$) where the substitution is on the phenyl ring, haloalkyl ($C_1$ to $C_6$) substituted phenylalkyl ($C_1$ to $C_6$) where the substitution is on the phenyl ring, alkoxy ($C_1$ to $C_6$) substituted phenylalkyl ($C_1$ to $C_6$) where the substitution is on the phenyl ring, halogen substituted phenylalkyl ($C_1$ to $C_6$) where the substitution is on the phenyl ring, and

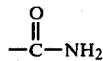

with the proviso that at least one $R_2$ is other than hydrogen or

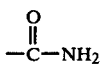

In another preferred subclass of the present invention, each $R_2$ is a radical independently selected from the group consisting of hydrogen, phenyl, benzyl, phenethyl, phenylpropyl, phenylbutyl, mono-alkyl ($C_1$ to $C_4$) substituted phenyl, monohaloalkyl ($C_1$ to $C_4$) substituted phenyl, mono-alkoxy ($C_1$ to $C_4$) substituted phenyl, mono-halogen substituted phenyl, monoalkyl ($C_1$ to $C_4$) substituted phenylalkyl ($C_1$ to $C_4$) where the substitution is on the phenyl ring, mono-haloalkyl ($C_1$ to $C_4$) substituted phenylalkyl ($C_1$ to $C_4$) where the substitution is on the phenyl ring, mono-alkoxy ($C_1$ to $C_4$) substituted phenylalkyl ($C_1$ to $C_4$) where the substitution is on the phenyl ring, mono-halogen substituted phenylalkyl ($C_1$ to $C_4$) where the substitution is on the phenyl ring, and

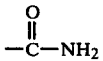

with the proviso that at least one $R_2$ is other than hydrogen or

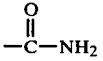

In a further preferred subclass of the present invention, each $R_2$ is a radical independently selected from the group consisting of hydrogen, phenyl, benzyl, phenethyl, mono-methyl substituted phenyl, mono-trifluoromethyl substituted phenyl, mono-methoxy substituted phenyl, mono-fluoro substituted phenyl, monochloro substituted phenyl, mono-methyl substituted benzyl where the substitution is on the phenyl ring, mono-trifluoromethyl substituted benzyl where the substitution is on the phenyl ring, mono-alkoxy substituted benzyl where the substitution is on the phenyl ring, mono-fluoro substituted benzyl where the substitution is on the phenyl ring, mono-chloro substituted benzyl where the substitution is on the phenyl ring, and

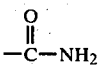

with the proviso that at least one $R_2$ in each formula is other than hydrogen or $$-\overset{\overset{\displaystyle O}{\|}}{C}-NH_2$$

Among the novel compounds of the present invention are, for example, 2,5-O-bis(o-tolyl)isoidide, 2-O-phenylisosorbide, 2,5-O-bis(m-trifluoromethylbenzyl)isosorbide, 2-O-(m-trifluoromethylbenzyl)isosorbide, 5-O-(m-trifluoromethylbenzyl)isosorbide, 5-O-(m-trifluoromethylbenzyl)isosorbide carbamate, 2,5-O-bis(o-trifluoromethylbenzyl)isosorbide, 2,5-O-bis(m-trifluoromethyl-3-phenylpropyl)isosorbide, 2-O-(o-trifluoromethylbenzyl)isosorbide, 2-O-(m-trifluoromethyl-3-phenylpropyl)isosorbide, 2-O-(m-trifluoromethylbenzyl)isomannide, 2-O-(m-trifluoromethylbenzyl)isoidide, 2-O-(m-trifluoromethylphenyl)isosorbide, 2-O-(p-trifluoromethylbenzyl)isosorbide, 2-O-(o-chlorobenzyl)isosorbide, 2-O-(phenyl)isosorbide, 2-O-(o-tolyl)isosorbide, 2,5-O-bis(phenyl)isoidide, 2-O-(p-chlorobenzyl)isosorbide, 2-O-(m-chlorobenzyl)isosorbide, 5-O-(o-chlorobenzyl)isosorbide, 2,5-O-bis(m-trifluoromethylbenzyl)isomannide, 2,5-O-bis(m-trifluoromethylbenzyl)isoidide, 2,5-O-bis(m-trifluoromethyl-3-phenylpropyl)isosorbide, 3,4-O-bis(m-trifluoromethylbenzyl)threitan.

The present invention also includes pharmaceutical compositions and the method of treating animals to obtain relaxation of their skeletal muscles composed of the novel compounds of the present invention as well as non-novel compounds, all of which (both novel and non-novel) compounds are represented by the general formulas:

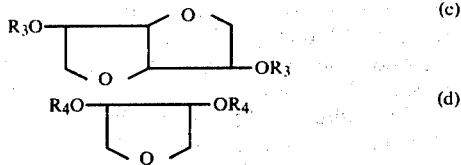

wherein each $R_3$ and $R_4$ is a radical independently selected from the group consisting of hydrogen, aryl, aralkyl, alkyl substituted aryl, haloalkyl substituted aryl, alkoxy substituted aryl, halogen substituted aryl, alkyl substituted aralkyl, haloalkyl substituted aralkyl, alkoxy substituted aralkyl, halogen substituted aralkyl, and

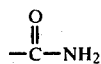

in each formula with the proviso that at least one $R_3$ and $R_4$ is other than hydrogen or

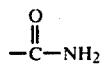

Among the non-novel compounds which are included within the present invention are 2,5-O-bis(3,4-dichlorobenzyl)isosorbide, 2-O-(2,4-dichlorobenzyl)isosorbide, 2,5-O-bis(benzyl)isosorbide, 2-O-benzyl isosorbide, 2-O- or 5-O-(3,4-dichlorobenzyl)isosorbide, 2,5-O-bis(2,4-dichlorobenzyl)isosorbide, and mixtures of such mono- and diethers or isosorbide.

The ethers of the invention can be prepared by etherifying an isohexide (e.g., isosorbide, isomannide or isoidide) or tetrahydrofuran with an appropriate etherifying reaction using conventional conditions. In view of the geometry of the isosorbide molecule, an endo- and an exo- hydroxy group, two isomeric monoethers are possible and are usually obtained together. These isomers can be conveniently separated by distillation or other conventional techniques. The invention contemplates the use of the separated isomeric forms of the mono-ether as well as mixtures thereof. In a typical preparation, benzyl chloride, o-chlorobenzyl chloride, 2,4-dichlorobenzyl chloride or 3,4-dichlorobenzyl chloride is reacted with isosorbide in the presence of aqueous sodium hydroxide to obtain one or more of the ethers of the invention, e.g., a mixture of the endo- and exo- mono-ethers and the diethers.

It is to be noted that the isohexides (isosorbide, isomannide and isoidide) are prepared by the dianhydrization of sorbitol, D-mannitol and L-iditol under acidic conditions. Isoidide has also been obtained from the isomerization of isosorbide with nickel catalyst. The isohexides have a common nucleus which consists of two nearly planar cis-fused tetrahydrofuran rings inclined to one another at an angle of about 120° resulting in the shape of a V or partially opened book. The configuration of the hydroxyl groups at the 2 and 5 positions (corresponding to the 2 and 5 positions of the initial hexitol) differentiates the isohexides. When the hydroxyl group is located inside the V it is designated as being in the endo configuration and when it is outside of the V it is in the exo configuration. Isosorbide has one hydroxyl group in the exo configuration and the other hydroxyl group in the endo configuration, isomannide has both hydroxyl groups in the endo configuration and in isoidide, both hydroxyl groups occupy the exo configuration. By convention the hydroxyl group attached to the 2 position of isosorbide is said to be in the exo configuration and the hydroxyl group in the 5 position occupies the endo configuration.

The configuration of an isohexide derivative is determined by the mechanism of the reaction involved in its formation. Reactions which proceed by cleavage of the oxygen hydrogen bond of the hydroxyl group in the 2 or 5 positions with substitution of a radical for the hydrogen atom result in products which have the same configuration as the reactant (i.e., the reactions proceed with retention of configuration). Esterification and ether formation are examples of reactions which proceed by this mechanism and consequently retention of configuration results. When the mechanism of the reaction involves rupture of the carbon oxygen bond at the 2 or 5 positions the reaction can theoretically proceed with retention or inversion of configuration (i.e., the new group has the opposite configuration of that occupied by the displaced radical). Displacement of the tosyloxy groups in isosorbide ditosylate results in an isosorbide derivative, but in the case of isomannide ditosylate and isoidide ditosylate the products have the isoidide and isomannide configurations respectively. Replacement of the tosyloxy group in isosorbide monotosylate results in the formation of an isomannide or isoidide derivative depending on the configuration of the isosorbide monotosylate. Application of this reaction to isomannide monotosylate and isoidide monotosylate results in the formation of isosorbide derivatives in which the substituent occupies the exo (2) position and the endo (5) position, respectively.

Representative of the compounds embraced by the present invention are:

1. Endo- and exo- mono-O-(m-trifluoromethylbenzyl)isosorbide isomers and their carbamates.

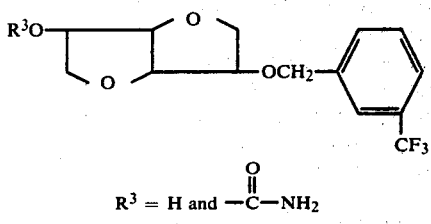

2. Ortho and para trifluoromethylbenzyl ethers of isosorbide and their carbamates.

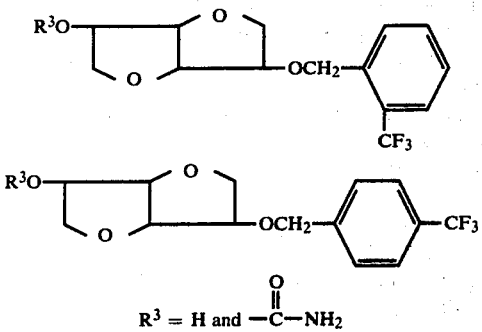

3. Mono-O-(m-trifluoromethylphenethyl)isosorbide and mono-O-(m-trifluoromethylphenylpropyl)isosorbide and their carbamates.

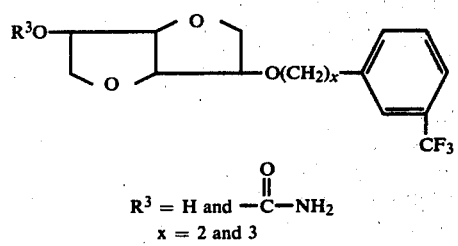

4. Substituted monobenzyl ethers of isosorbide with chloro, methoxy, nitro and methyl groups in the ortho, meta and para positions.

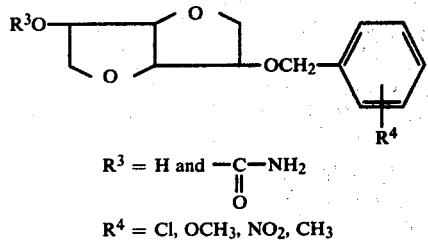

The invention is illustrated, but not limited, by the following examples:

EXAMPLE 1

2- and 5-O-(o-chlorobenzyl)isosorbide o-Chlorobenzyl chloride (161 g, 1 mole) was reacted with the sodium salt of isosorbide [prepared from isosorbide (876 g, 6 moles) and 24 g, 1 mole of sodium hydride (50% dispersion in mineral oil) in 1500 ml of dimethyl sulfoxide] at 70°–71° C. for 1 hour. The reaction mixture was concentrated under reduced pressure. 1500 ml of water was added to the concentrated mixture. After acidifying the mixture with 2 N hydrochloric acid, the mixture was extracted with diethyl ether (4×200 mls). The ether extracts were combined, washed with water (2×600 mls), and dried overnight over anhydrous sodium sulfate. The dried ether solution was filtered and the ether stripped from the filtrate under reduced pressure. 261.4 g of pot residue formed two layers. Separation of the layers gave 15.6 g of mineral oil (top layer) and 242.3 g of dark brown viscous liquid. Approximately 221 g of a mixture of 2-O- and 5-O-(o-chlorobenzyl)isosorbides and 13 g of 2,5-O-bis-(o-chlorobenzyl)isosorbide were separated by column chromatography (silica gel column eluted with ether). Some of the 2-O isomer was separated from the 5-O isomer by repeating the column chromatography. Additional 5-O isomer was separated from mixtures of the 2-O and 5-O isomers (containing at least 80% 5-O isomer) by recrystallizing with ether.

EXAMPLE 2

2-O-phenylisosorbide

Isomannide monotosylate (150 g, 0.5 mole) dissolved in 800 ml of triethylene glycol dimethyl ether was reacted with sodium phenoxide [prepared from phenol (47 g, 0.5 mole) and sodium (11.5 g, 0.5 mole) in 200 ml of triethylene glycol dimethyl ether] at 138°–140° C. for 3 hours. After standing overnight at room temperature, the reaction mixture was filtered. The filter cake was washed with diethyl ether and filtered. Above filtrates were combined and the solvents stripped under reduced pressure. The pot residue was stirred with boiling ethanol and filtered. Approximately 15 g of 2,5-O-bis-phenylisoidide was obtained after cooling the filtrate (some isomannide ditosylate impurity in the starting monotosylate). Distillation of the filtrate gave approximately 52 g of 2-O-phenylisosorbide.

EXAMPLE 3

2- and 5-O-(m-trifluoromethylbenzyl)isosorbide m-Trifluoromethylbenzyl chloride (58.35 g, 0.3 mole) was reacted with a mixture of sodium hydroxide (12 g, 0.3 mole) in 50 ml of water and isosorbide (18.25 g, 0.125 mole) at 108°–116° C. for 9 hours. The reaction mixture was acidified with hydrochloric acid. 50 ml of water was added to the mixture and extracted with diethyl ether (2×50 ml). The ether extracts were washed with water (2×50 ml) and dried over anhydrous sodium sulfate. The dried ether solution was filtered and the ether stripped off leaving 61.9 g of pot residue. Distillation of the pot residue gave 13 g of a mixture of 2-O- and 5-O-(m-trifluoromethylbenzyl)isosorbide, 3.5 g of 2,5-O-bis(m-trifluoromethylbenzyl)isosorbide, and 31 g of unreacted m-trifluoromethylbenzyl chloride.

EXAMPLE 4

5-O-(m-trifluoromethylbenzyl)isosorbide carbamate

5-O-(m-trifluoromethylbenzyl)isosorbide (12 g, 0.039 mole) and sodium cyanate (5.1 g, 0.078 mole) in 30 ml of methylene chloride was treated at 26°–27° C. with dropwise addition of trifluoroacetic acid (8.9 g, 0.078 mole) over a period of an hour. After stirring the reaction mixture overnight, the mixture was warmed to 30° C. and stirred for 4 more hours. 250 ml of water was added to the reaction mixture with stirring, allowed to stand until solids formed and filtered. The filter cake was washed with water and then dissolved in 150 ml of 90% ethanol. This ethanol solution was treated with DARCO G-60, warmed to boiling and filtered. Approximately 25 ml of water was added to the filtrate with stirring, allowed to stand until crystallization occurred and filtered. Approximately 6.4 g of 5-O-(m-trifluoromethylbenzyl)isosorbide carbamate was obtained.

Further compounds according to the invention and their preparation are described in the following Table I wherein the "Method Used" refers to the methods illustrated by corresponding numbered Examples 1 to 4.

ISOHEXIDE MONOETHERS

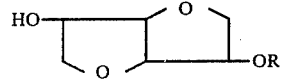

| R | Isohexide Isomer* | Method Used | M.P. or B.P. (°C.) | Yield (%) | Found (%) C | H | F | Calculated (%) C | H | F |
|---|---|---|---|---|---|---|---|---|---|---|
| m-CF$_3$C$_6$H$_4$CH$_2$— | A | I | 149–151 (0.22 mm) | 53 | 55.37 | 4.68 | 19.05 | 55.27 | 4.97 | 18.73 |
|  | A | III | 158–160 (0.65 mm) | 14 | 55.43 | 5.75 | 18.50 | 55.27 | 4.97 | 18.73 |
| o-CF$_3$C$_6$H$_4$CH$_2$— | A | I | — | 84 | 54.84 | 5.02 | 18.98 | 55.27 | 4.97 | 18.73 |
| m-CF$_3$C$_6$H$_4$(CH$_2$)$_3$— | A | I | — | 73 | 58.16 | 5.19 | 16.81 | 57.83 | 5.76 | 17.15 |
| m-CF$_3$C$_6$H$_4$CH$_2$— | B | I | 161–162 (0.7 mm) | 39 | 54.96 | 4.96 | 19.29 | 55.27 | 4.97 | 18.73 |
| m-CF$_3$C$_6$H$_4$CH$_2$— | C | I | 166–169 (0.17 mm) | 24 | 55.46 | 4.83 | 19.03 | 55.27 | 4.97 | 18.73 |
| m-CF$_3$C$_6$H$_4$— | A | II | 131–133 (0.25 mm) | 29 | 53.94 | 4.42 | 20.05 | 53.79 | 4.51 | 19.64 |
|  |  | II$^a$ | 51–57 | 47 | 54.12 | 4.23 | 19.83 | 53.79 | 4.51 | 19.64 |
| p-CF$_3$C$_6$H$_4$CH$_2$— | A | I |  | 95 | 54.87 | 5.12 | 18.87 | 55.27 | 4.97 | 18.73 |
| C$_6$H$_5$CH$_2$— | A | III | 98–99.5 | — | 66.65 | 6.83 | — | 66.08 | 6.83 | — |

*A = isosorbide
B = isomannide
C = isoidide
$^a$Dimethyl sulfoxide used as solvent.

ISOHEXIDE MONOETHERS

| R | Isohexide Isomer* | Method Used | M.P. (°C.) | Yield (%) | Found (%) C | H | N | Halogen | Calculated (%) C | H | N | Halogen |
|---|---|---|---|---|---|---|---|---|---|---|---|---|
| C$_6$H$_5$— | A | II | 52.5–55.0 | 47 | 65.12 | 6.38 | — | — | 64.85 | 6.35 | — | — |
| o-CH$_3$C$_6$H$_4$— | A | II | 100.5–102 | 35 | 66.16 | 6.79 | — | — | 66.08 | 6.83 | — | — |
| o-ClC$_6$H$_4$CH$_2$— | A | I | — | 82 | 57.93 | 5.79 | — | 13.18$^d$ | 57.68 | 5.59 | — | 13.10$^d$ |
| m-ClC$_6$H$_4$CH$_2$— | A | I | — | 54 | 57.70 | 5.77 | — | 13.19$^d$ | 57.68 | 5.59 | — | 13.10$^d$ |
| p-ClC$_6$H$_4$CH$_2$— | A | I | — | 72 | 57.83 | 5.52 | — | 13.33$^d$ | 57.68 | 5.59 | — | 13.10$^d$ |

ISOHEXIDE MONOETHER CARBAMATES

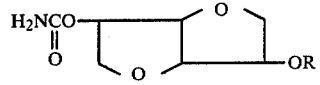

| R | Isohexide Isomer* | Method Used | M.P. (°C.) | Yield (%) | Found (%) C | H | N | Halogen | Calculated (%) C | H | N | Halogen |
|---|---|---|---|---|---|---|---|---|---|---|---|---|
| o-ClC$_6$H$_4$CH$_2$—$^b$ | A | IV | 135–137 | 11 | 53.83 | 5.22 | 4.52 | 11.05$^d$ | 53.60 | 5.14 | 4.46 | 11.30$^d$ |
| o-ClC$_6$H$_4$CH$_2$—$^c$ | A | IV | 141–143 | 19 | 53.83 | 5.27 | 4.46 | 11.04$^d$ | 53.60 | 5.14 | 4.46 | 11.30$^d$ |
| m-CF$_3$C$_6$H$_4$—CH$_2$—$^b$ | A | IV | 146–147.5 | 25 | 51.65 | 4.94 | 3.89 | 16.48$^e$ | 51.88 | 4.64 | 4.03 | 16.41$^e$ |
| m-CF$_3$C$_6$H$_4$—CH$_2$—$^c$ | A | IV | 112–114 | 47 | 51.79 | 4.46 | 3.82 | 16.79$^e$ | 51.88 | 4.64 | 4.03 | 16.41$^e$ |

*A = isosorbide
$^b$2-O isomer
$^c$5-O isomer
$^d$chlorine
$^e$fluorine

ISOHEXIDE DIETHERS

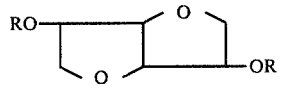

| R | Isohexide* Isomer | Method Used | M.P. or B.P. (°C.) | Yield (%) | Found (%) C | H | F | Calculated (%) C | H | F |
|---|---|---|---|---|---|---|---|---|---|---|
| m-CF$_3$C$_6$H$_4$CH$_2$— | A | I | 213–215 | 57 | 57.47 | 4.26 | — | 57.15 | 4.35 | 24.65 |

-continued

ISOHEXIDE DIETHERS

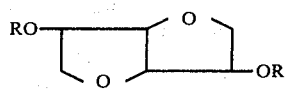

| R | Isohexide* Isomer | Method Used | M.P. or B.P. (°C.) | Yield (%) | Found (%) C | H | F | Calculated (%) C | H | F |
|---|---|---|---|---|---|---|---|---|---|---|
|  |  | III | (0.83 mm) 222–224 (0.95 mm) | 5 | 57.52 | 4.01 | 24.60 | 57.15 | 4.35 | 24.65 |
| o-CH$_3$C$_6$H$_4$— | C | II | 85.5–86.5 | 37 | 73.92 | 6.92 | — | 73.60 | 6.79 | — |
| C$_6$H$_5$— | C | II | 109–111 | 33 | 72.06 | 6.03 | — | 72.46 | 6.08 | — |
| m-CF$_3$C$_6$H$_4$CH$_2$— | B | I | 70–72 | 4$^a$ | 56.90 | 4.39 | 25.21 | 57.15 | 4.35 | 24.65 |
| m-CF$_3$C$_6$H$_4$CH$_2$— | C | I | 195–200 (0.2 mm) | 10$^a$ | 57.16 | 4.08 | 24.90 | 57.15 | 4.35 | 24.65 |
| p-CF$_3$C$_6$H$_4$CH$_2$— | A | I | — | 6$^a$ | — | — | — | — | — | — |
| o-CF$_3$C$_6$H$_4$CH$_2$— | A | I | — | 6$^a$ | — | — | — | — | — | — |
| m-CF$_3$C$_6$H$_4$(CH$_2$)$_3$— | A | I | — | 3$^a$ | — | — | — | — | — | — |
| o-ClC$_6$H$_4$CH$_2$— | A | I | — | 7$^a$ | — | — | — | — | — | — |
| m-ClC$_6$H$_4$CH$_2$— | A | I | — | 5$^a$ | — | — | — | — | — | — |

*A = isosorbide
B = isomannide
C = isoidide
$^a$Isolated as by-product from monoether synthesis.

TETRAHYDROFURAN ETHERS

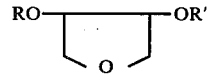

| R | R' | Tetrahydrofuran Isomer | Method Used | B.P. (°C) | Yield (%) | Found (%) C | H | F | Calculated (%) C | H | F |
|---|---|---|---|---|---|---|---|---|---|---|---|
| m-CF$_3$C$_6$H$_4$CH$_2$— | H | Erythritan | I | — | 82 | 54.92 | 4.68 | 21.89 | 54.96 | 5.0 | 21.74 |
| m-CF$_3$C$_6$H$_4$CH$_2$— | H | Threitan | I | 117–118 (0.075 mm) | 50 | 54.86 | 4.94 | 22.31 | 54.96 | 5.0 | 21.74 |
| m-CF$_3$C$_6$H$_4$CH$_2$— | m-CF$_3$C$_6$H$_4$CH$_2$— | Erythritan | I | 165–166 (0.27 mm) | 29 | 57.35 | 4.00 | 27.16 | 57.15 | 4.31 | 27.12 |
| m-CF$_3$C$_6$H$_4$CH$_2$— | m-CF$_3$C$_6$H$_4$CH$_2$— | Threitan | I | 165–167 (0.1 mm) | 29 | 56.92 | 3.86 | 27.29 | 57.15 | 4.31 | 27.12 |

Evaluation in laboratory animals indicates that the compounds of this invention (both novel and non-novel) may be used by administering a therapeutically effective amount thereof to a warm-blooded living animal or mammal, in need of skeletal muscle relaxation or other form of central nervous system depression. The dosage required varies, as is customary in this art, with the species being treated, weight of the animal and route of administration. The active compound may be administered in the form of pharmaceutical compositions comprising an effective amount of at least one of the indicated compounds or non-toxic, pharmaceutically acceptable acid-addition salt thereof, in combination with a pharmaceutically acceptable diluent or carrier. A suitable composition is, for example, a tablet, capsule, aqueous or oily emulsion suspension or solution, injectable aqueous or oil solution or suspension, dispersible powder, spray or aerosol.

Preferred oral dosage forms are tablets or capsules containing between 10 mg to 5000 mg, preferably 30 mg to 1000 mg of active ingredient. Preferred parenteral dosage forms are sterile aqueous solutions containing between 0.05% and 1% w/v of active ingredient. In accordance with the present invention, the subject compounds are administered at doses from about 0.5 mg/kg to 400 mg/kg body weight at 4–6 hourly intervals. A more preferred dose is from about 1 milligram to 200 milligrams per kilogram body weight at 4–6 hour intervals.

The pharmacological activity of the present compounds is demonstrated below:

EXAMPLE 5

This example illustrates the muscle relaxant activity of two representative compounds according to the invention.

Anticonvulsant Activity in Mice

The test used involved injecting mice weighing 18–22 grams intraperitoneally with the drug candidate, and $\frac{1}{2}$ hour later giving the mice a supramaximal electro-shock, or a subcutaneous injection of strychnine. The number of animals which have convulsions in response to these challenges is noted, and compared to control groups which are pretreated only with water.

The compound isosorbide mono-m-trifluoromethyl-benzyl ether, at 200 mg/kg, was tested in this way and was found to protect 100% against electro-shock and 33% against strychnine siezures. These data indicate depression of the neuromotor system in a manner similar to classical muscle relaxants.

Spinal Reflexes of the Cat

For this test, cats weighing 2–4 kg were anesthetized with Dial-urethane and placed on artificial respiration.

One hindlimb was fixed by a bone clamp around the femur, and the patellar reflex was elicited by tapping the knee with a Palmer solenoid driven hammer. The linguomandibular (jaw-opening) reflex was elicited by electrically stimulating the tongue via needle electrodes on either side of the frenulum. The drugs tested were dissolved in propylene glycol and injected into the brachial vein. Responses were monitored with a Beckman Dynograph.

The compound 2- and 5-O-(o-chlorobenzyl)isosorbide was found to reduce the linguomandibular reflex on an average of about 50% at a dose of 10 mg/kg. At this dose, and even higher doses, there is no significant effect upon the patellar reflex. Those data indicate that the test compound acts selectively on polysynaptic spinal reflexes in a manner similar to classical muscle relaxants.

The compounds of the present invention exhibit central nervous system depression activity and more secifically demonstrate skeletal muscle relaxant effects. Anticonvulsant, anti-tremor, analgesic and tranquilizer activity is also shown by certain of these compounds.

Examples of pharmaceutical formulations of the present invention are as follows:

| Tablet Containing 100 mg of 2,5-0-bis(3,4-dichlorobenzyl)isosorbide | 1000 Tablets (Grams) |
| --- | --- |
| 2,5-0-bis(3,4-dichlorobenzyl)isosorbide | 100 |
| Starch | 80 |
| Powdered Lactose | 80 |
| Talc | 20 |
| Weight of Granulation | 280 |

Combine all ingredients, mix and then compress into slugs. The slugs should then be ground to form granules that will pass a 14 to 16 mesh screen. The granules may then be recompressed into tablets using a suitable compression mold to form tablets, each weighing 280 mg.

| Suspension Containing 50 mg/5 cc of 2-0-(benzyl)isosorbide | |
| --- | --- |
| 2-0-(benzyl)isosorbide | 10 grams |
| Tragacanth | 50 grams |
| Amaranth | 10 grams |
| Syrup Cherry | 60 ml |
| Distilled Water q.s. | 1000 ml |

Hydrate the tragacanth with sufficient water to form a smooth paste and to this add the 2-O-(benzyl)isosorbide, followed by the amaranth which has been previously dissolved in water. Then add the syrup of cherry and distilled water to make 1000 ml.

| Injectable Containing 10 mg of 2-0-(o-chlorobenzyl)isosorbide Per Milliliter Suitable for Intramuscular, Intraperitoneal, or Subcutaneous Injection | |
| --- | --- |
| 2-0-(o-chlorobenzyl)isosorbide | 10.0 grams |
| Chlorobutanol | 3.0 grams |
| Propylene Glycol | 20.0 ml |
| Water for Injection q.s. | 1000.0 ml |

Having thus described our invention we claim:

1. A method of bringing about relaxation of skeletal musculature in a mammal comprising administering to a mammal therapeutically effective amount of a compound selected from the group consisting of those represented by the formulas:

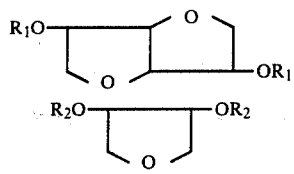

wherein each $R_1$ is a radical independently selected from the group consisting of hydrogen, aryl, aralkyl where the aralkyl radical contains from 9 to 12 carbon atoms, alkyl substituted aryl, haloalkyl substituted aryl, alkoxy substituted aryl, halogen substituted aryl, alkyl substituted aralkyl, haloalkyl substituted aralkyl, alkoxy substituted aralkyl, mono-halogen substituted aralkyl where the aralkyl radical contains from 7 to 12 carbon atoms, di- and tri-halogen substituted aralkyl where the aralkyl radical contains from 9 to 12 carbon atoms, and

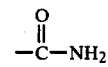

and each $R_2$ is independently selected from the group consisting of hydrogen, aryl, aralkyl, alkyl substituted aryl, haloalkyl substituted aryl, alkoxy substituted aryl, halogen substituted aryl, alkyl substituted aralkyl, haloalkyl substituted aralkyl, alkoxy substituted aralkyl, halogen substituted aralkyl, and

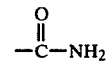

with the proviso that at least one $R_1$ and $R_2$ in each formula is other than hydrogen or

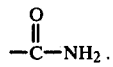

2. A method of bringing about relaxation of skeletal musculature in a mammal comprising administering to a mammal a therapeutically effective amount of a compound selected from the group consisting of those represented by the formula:

wherein each $R_1$ is a radical independently selected from the group consisting of hydrogen, phenyl, phenylalkyl ($C_3$ to $C_6$), alkyl ($C_1$ to $C_6$) substituted phenyl, haloalkyl ($C_1$ to $C_6$) substituted phenyl, alkoxy ($C_1$ to $C_6$) substituted phenyl, halogen substituted phenyl, alkyl ($C_1$ to $C_6$) substituted phenylalkyl ($C_1$ to $C_6$) where the substitution is on the phenyl ring, haloalkyl ($C_1$ to $C_6$) substituted phenyl alkyl ($C_1$ to $C_6$) where the substitution is on the phenyl ring, alkoxy ($C_1$ to $C_6$) substituted phenylalkyl ($C_1$ to $C_6$) where the substitution is on the phenyl ring, di- and tri-halogen substituted phenylalkyl ($C_3$ to $C_6$) where the substitution is on the phenyl ring, mono-halogen substituted benzyl where the substitution is on the phenyl ring, and

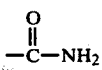

with the proviso that at least one $R_1$ is other than hydrogen or

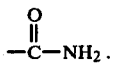

3. A method of bringing about relaxation of skeletal musculature in a mammal comprising administering to a mammal a composition comprised of a therapeutically effective amount of a compound selected from the group consisting of those represented by the formulas:

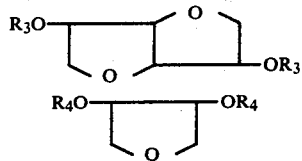

wherein each $R_3$ and $R_4$ is a radical independently selected from the group consisting of hydrogen, aryl, aralkyl, alkyl substituted aryl, haloalkyl substituted aryl, alkoxy substituted aryl, halogen substituted aryl, alkyl substituted aralkyl, haloalkyl substituted aralkyl, alkoxy substituted aralkyl, halogen substituted aralkyl, and

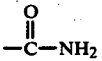

with the proviso that at least one $R_3$ and $R_4$ in each formula is other than hydrogen or

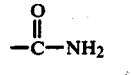

in a pharmaceutical carrier.

4. A method of claim 1 wherein each $R_1$ is a radical independently selected from the group consisting of hydrogen, phenyl, phenylpropyl, phenylbutyl, mono-alkyl ($C_1$ to $C_4$) substituted phenyl, mono-haloalkyl ($C_1$ to $C_4$) substituted phenyl, mono-alkoxy ($C_1$ to $C_4$) substituted phenyl, mono-halogen substituted phenyl, mono-alkyl ($C_1$ to $C_4$) substituted phenylalkyl ($C_1$ to $C_4$) where the substitution is on the phenyl ring, monohaloalkyl ($C_1$ to $C_4$) substituted phenylalkyl ($C_1$ to $C_4$) where the substitution is on the phenyl ring, mono-alkoxy ($C_1$ to $C_4$) substituted phenylalkyl ($C_1$ to $C_4$) where the substitution is on the phenyl ring, mono-halogen substituted phenylalkyl ($C_1$ to $C_4$) where the substitution is on the phenyl ring, and

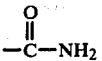

with the proviso that at least one $R_1$ is other than hydrogen or

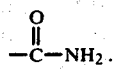

5. A method of claim 1 wherein each $R_1$ is a radical independently selected from the group consisting of hydrogen, phenyl, phenylpropyl, mono-methyl substituted phenyl, mono-trifluoromethyl substituted phenyl, mono-methoxy substituted phenyl, mono-fluoro substituted phenyl, mono-chloro substituted phenyl, mono-methyl substituted benzyl where the substitution is on the phenyl ring, mono-trifluoromethyl substituted benzyl where the substitution is on the phenyl ring, mono-alkoxy substituted benzyl where the substitution is on the phenyl ring, mono-fluoro substituted benzyl where the substitution is on the phenyl ring, mono-chloro substituted benzyl where the substitution is on the phenyl ring, and

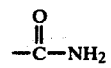

with the proviso that at least one $R_1$ is other than hydrogen or

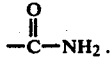

6. A method of bringing about relaxation of skeletal musculature in a mammal comprising administering to a mammal a therapeutically effective amount of a compound selected from the group consisting of those represented by the formula:

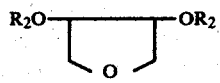

where each $R_2$ is a radical independently selected from the group consisting of hydrogen, phenyl, phenylalkyl ($C_1$ to $C_6$), alkyl ($C_1$ to $C_6$) substituted phenyl, haloalkyl ($C_1$ to $C_6$) substituted phenyl, alkoxy ($C_1$ to $C_6$) substituted phenyl, halogen substituted phenyl, alkyl ($C_1$ to $C_6$) substituted phenylalkyl ($C_1$ to $C_6$) where the substitution is on the phenyl ring, haloalkyl ($C_1$ to $C_6$) substituted phenylalkyl ($C_1$ to $C_6$) where the substitution is on the phenyl ring, alkoxy ($C_1$ to $C_6$) substituted phenylalkyl ($C_1$ to $C_6$) where the substitution is on the phenyl ring, halogen substituted phenylalkyl ($C_1$ to $C_6$) where the substitution is on the phenyl ring, and

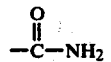

with the proviso that at least one $R_2$ is other than hydrogen or

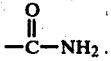

7. A method of claim 1 wherein the compound is 2-O-(o-chlorobenzyl)isosorbide.

8. A method of claim 1 wherein the compound is 5-O-(o-chlorobenzyl)isosorbide.

* * * * *